US009288993B2

(12) United States Patent
Manczinger et al.

(10) Patent No.: US 9,288,993 B2
(45) Date of Patent: Mar. 22, 2016

(54) **COPPER RESISTANT, FENGYCIN-PRODUCING *BACILLUS MOJAVENSIS* STRAIN FOR CONTROLLING VEGETABLE PATHOGENS, ITS USE AND COMPOSITIONS CONTAINING IT**

(75) Inventors: László Manczinger, Szeged (HU); Csaba Vágvölgyi, Szöreg (HU); Enikö Sajben, Szeged (HU); Árpád Nagy, Szeged (HU); Zoltán Szöke-Kis, Mezöberény (HU); Adrienn Nagy, Kecskemét (HU); György Turóczi, Gödöllö (HU); András Kovács, Kecskemét (HU)

(73) Assignee: Szegedi Tudományegyetem, Szeged (HU)

( * ) Notice: Subject to any disclaimer, the term of this patent is extended or adjusted under 35 U.S.C. 154(b) by 35 days.

(21) Appl. No.: 14/343,348

(22) PCT Filed: Aug. 30, 2012

(86) PCT No.: PCT/HU2012/000084
§ 371 (c)(1),
(2), (4) Date: May 27, 2014

(87) PCT Pub. No.: WO2013/034938
PCT Pub. Date: Mar. 14, 2013

(65) Prior Publication Data

US 2015/0147296 A1 May 28, 2015

(30) Foreign Application Priority Data

Sep. 8, 2011 (HU) .................................... 1100498

(51) Int. Cl.
*A01N 63/00* (2006.01)
*C12R 1/07* (2006.01)

(52) U.S. Cl.
CPC .. *A01N 63/00* (2013.01); *C12R 1/07* (2013.01)

(58) Field of Classification Search
CPC ..................................................... A01N 63/00
USPC .................................................... 424/93.462
See application file for complete search history.

(56) References Cited

U.S. PATENT DOCUMENTS 4,937,193 A * 6/1990 Hinchliffe et al. ............ 435/477
5,232,850 A * 8/1993 Casida, Jr. ................ 435/253.3

(Continued)

FOREIGN PATENT DOCUMENTS

| | | | |
|---|---|---|---|
| WO | 98/21964 | A1 | 5/1998 |
| WO | 99/09834 | A2 | 3/1999 |
| WO | 2011/121408 | A1 | 10/2011 |

OTHER PUBLICATIONS

Vagvolgyi, C et al, Cereal Research Communications, 2009, vol. 37, Suppl. 1, pp. 539-592, The effect of copper on the effectiveness of biocontrol bacterium strains.*

Maheshwari, D.K. Bacteria in Agrobiology:;CropEcosystems, pp. 21-39, Bacillus mojavensis: It's endophytic nature, the surfactins and their Role in the Plant Response to Infection by Fusarium verticillioides, Chapter 2, Charles W. Bacon et al.*

(Continued)

*Primary Examiner* — Albert Navarro
*Assistant Examiner* — Ginny Portner
(74) *Attorney, Agent, or Firm* — Jason D. Voight

(57) ABSTRACT

A biological material is disclosed for exerting antagonism against vegetable pathogens, which contains *Bacillus mojavensis* R3B mutant strain deposited under # NCAIM (P) B 001389 according to the Budapest Treaty. The biological material according to the invention is an effective antagonist against the pathogens of vegetables, preferably tomato, pepper, lettuce and/or cabbage, in particular against the pathogens selected from the group of *Xanthomonas vesicatoria, Pseudomonas syringae* and *Clavibacter michiganensis* vegetable pathogen bacteria and *Pythium debaryanum, Phytophthora infestans, Alternaria alternata* and *Fusarium oxysporum* vegetable pathogen fungi. Furthermore, the invention relates to a composition comprising the biological material according to the invention and optionally a copper-containing pesticide and a process for controlling vegetable pathogens, furthermore use of the biological material or composition according to the invention for the protection of vegetables, preferably tomato, pepper, lettuce and/or cabbage.

18 Claims, 4 Drawing Sheets

(56) References Cited

U.S. PATENT DOCUMENTS

| | | | |
|---|---|---|---|
| 5,637,504 A * | 6/1997 | Hinchliffe et al. | 435/69.1 |
| 5,994,117 A | 11/1999 | Bacon et al. | |
| 6,103,519 A * | 8/2000 | Comberbach et al. | 435/320.1 |
| 6,319,497 B1 * | 11/2001 | Casida et al. | 424/93.47 |
| 6,325,934 B1 * | 12/2001 | Tobey, Jr. | C02F 3/34 210/606 |
| 9,185,915 B2 * | 11/2015 | Guilhabert-Goya | A01N 63/00 |
| 2003/0166256 A1 * | 9/2003 | Zahn | A01N 63/02 435/252.4 |
| 2004/0171519 A1 * | 9/2004 | DiSpirito et al. | 514/6 |
| 2005/0287146 A1 * | 12/2005 | Patti et al. | 424/151.1 |
| 2007/0224179 A1 | 9/2007 | Jacobsen et al. | |
| 2009/0042267 A1 * | 2/2009 | Park | B01F 7/0025 435/170 |
| 2010/0092442 A1 * | 4/2010 | Jacobsen | A01N 63/00 424/93.46 |
| 2011/0110894 A1 * | 5/2011 | Drahos | C02F 3/1268 424/93.3 |
| 2011/0287467 A1 * | 11/2011 | Crane | C07K 14/795 435/25 |
| 2012/0231951 A1 * | 9/2012 | Guilhabert-Goya | C07K 14/32 504/101 |
| 2013/0096003 A1 | 4/2013 | Fernandez Martinez et al. | |
| 2013/0172184 A1 * | 7/2013 | Bain et al. | 504/100 |
| 2014/0323305 A1 * | 10/2014 | Rheinheimer | A01N 37/50 504/206 |
| 2014/0336221 A1 * | 11/2014 | Pegan et al. | 514/314 |

OTHER PUBLICATIONS

Samel, SA et al, Journal of Molecular Biology, 2006, vol. 359, pp. 876-889, The Thioesterase Domain of the Fengycin Biosynthesis Cluster: A Structural Base for the Macrocyclization of a Non-ribosomal Lipopeptide.*

Steller, S et al, Journal of Chromatography B, vol. 737, 2000, pp. 267-275, Purification of the fengycin synthetase multienzyme system from Bacillus subtilis b213.*

Weed, Lawrence L., Effects of Copper on Bacillus subtilis, Journal of Bacteriology, pp. 1003-1010, vol. 85, 1963.*

Steller, S et al, Chemistry and Biology, Jan. 1999, vol. 6, pp. 31-41, Structural and functional organization of the fengycin synthetase multienzyme system from Bacillus subtilis b213 and A1/3.*

Lin, Tsyey-Pin et al, Biochimica et Biophysica Acta, vol. 1730, 2005, pp. 159-164, Functional analysis of fengycin synthetase FenD.*

Kim, Pyoung II et al, J. Microbiol. Biotechnol., 2010, vol. 20(1), pp. 138-145, Production of Biosurfactant Lipopeptides Iturin A, Fengycin and Surfactin A from Bacillus subtilis CMB32 for control of Colletotrichum gloeosporioides.*

Bacon, Charles W. et al, Chapter 2, Bacillus mojavensis:Its Endophytic Nature, the Surfactins, and Their Role in the Plant Response to Infection by Fusarium verticillioides, in Bacteria in Agrobiology, Plant Growth Responses, pp. 21-39.*

Vágvölgyi et al.: "The effect of copper on the effectiveness of biocontrol bacterium strains", Cereal Research Communications, 2009, abstract.

* cited by examiner

AM= the nitrogen source is ammonium chloride, NM= the nitrogen source is sodium nitrate; yeast= the nitrogen source is yeast extract;

The evaluation was done with Suc-Ala-Ala-Pro-Phe-pNA chromogenic substrate.

US 9,288,993 B2

COPPER RESISTANT, FENGYCIN-PRODUCING *BACILLUS MOJAVENSIS* STRAIN FOR CONTROLLING VEGETABLE PATHOGENS, ITS USE AND COMPOSITIONS CONTAINING IT

This is the national stage of International Application PCT/HU2012/000084, filed Aug. 30, 2012.

BRIEF DESCRIPTION OF THE INVENTION

The invention relates to a biological material for exerting antagonism against vegetable pathogens, which contains *Bacillus mojavensis* R3B mutant strain deposited on Aug. 8, 2011 at the National Collection of Agricultural and Industrial Microorganisms, Somlói ut 14-16, 1118 Budapest, Hungary, under accession number NCAIM (P) B 001389 according to the Budapest Treaty. The biological material according to the invention is an effective antagonist against the pathogens of vegetables, preferably tomato, pepper, lettuce and/or cabbage, in particular against the pathogens selected from the group of *Xanthomonas vesicatoria, Pseudomonas syringae* and *Clavibacter michiganensis* vegetable pathogen bacteria and *Pythium debaryanum, Phytophthora infestans, Alternaria alternata* and *Fusarium oxysporum* vegetable pathogen fungi. Furthermore, the invention relates to a composition comprising the biological material according to the invention and optionally a copper-containing pesticide and a process for controlling vegetable pathogens, furthermore use of the biological material or composition according to the invention for the protection of vegetables, preferably tomato, pepper, lettuce and/or cabbage.

BACKGROUND OF THE INVENTION

The effective pest control is part of the intensive vegetable production technologies, however, the expectations of the consumer markets, furthermore the efforts to improve the food safety called for the minimization of pesticides, and replacing them by biological methods. In a closed area production the entire biological control has been achieved against insect pests, however, the biological control of bacteria and fungi is still to be elaborated.

Nowadays there is an increasing need in the fields of vegetable production and sales for bioproducts containing no residues of chemical pesticides. Among the effective chemical pesticides only the inorganic copper-compositions are allowed in the course of production of bioproducts. The number of copper resistant mutants among the vegetable pathogen microorganisms has increased a lot in the last couple of years, thus these copper containing agents alone are insufficient to achieve effective and reliable pest control. One possible solution to overcome this problem is to effect an integrated pest control using copper containing agents and biocontol compositions. Biocontrol products may also be used alone, but in such cases the highest efficiency of the best compositions is still under 50 percent.

The majority of the antibacterial or antifungal biocontrol products presently available in the world market contain one component as active agent, which is a bacterium or fungi possessing antagonist and/or parasite features. The *Bacillus* strain has long been used for vegetable pest control purposes. The compositions sold are especially effective against vegetable pathogen fungi. The compositions already been commercialized and patented comprise mainly the strains of *Bacillus subtilis* and *Bacillus amiloliquefaciens* species. Their effectiveness is explained by different peptide antibiotics, secreted outside of the cell walls, which are effective mainly against fungi: surfactin, iturin, fengycin, bacillomycin, mycosubtilin. Recently it has been suggested that their effectiveness is enhanced by extracellular enzymes decomposing the cell walls and/or the membrane of the cytoplasm of the pathogen microorganism: proteases, kitinases and lipases. Besides, several independent investigations have proved that of the secreted antibiotics mainly fengycin is responsible for exerting of the induced resistance response in the treated plants.

THE STATE OF THE ART

U.S. Pat. No. 2010092442 relates to a process to induce an acquired systemic resistance of plants against infections. The method is based on the utilization of a composition comprising bacteria belonging to the *Bacillus* strain, as a consequence of which the plant produces protecting proteins. The applied bacteria are the isolate of *Bacillus mojavensis* 203-7-, and the isolate of *Bacillus mycoides* BmJ. The drawback of the *Bacillus mojavensis* isolate are on one hand that the application of the given *Bacillus mojavensis* 203-7 isolate and the antibacterial agent together is not proposed, on the other hand, the isolated strain is not copper resistant, thus the combined application thereof with copper-containing pesticides would not achieve the expected pest control effect. Furthermore, the *Bacillus mojavensis* 203-7 isolate disclosed in the patent has no fengycin hyper-producing properties.

International patent application No. WO9724433 discloses biocontrol methods and microorganisms, which are capable of controlling plant diseases of fungi origin. The microorganisms useful for biocontrol purposes are novel endophyte symbiotic *Enterobacter cloacae* strains. Said strains are suitable for passing useful genetic products into the plants. The used *Enterobacter cloacae* strains are rifampicin resistant. The *Enterobacter cloacae* strains according to the patent application (deposited under No. ATCC55732) as analysed their 16S rRNS gene sequence have proven to be *Bacillus mojavensis* strains. The shortcoming of the isolate according to the patent application is that it has no copper resistance, therefore its co-application with copper containing pesticides is likely to be discouraged.

International patent application No. WO9909834 discloses compositions and methods for the treatment of arable soil, which are capable of improving the growth of plants and the results of reaping. The composition is based on pesticide resistant microorganism strains. One strain or a mixture of several strains among the microorganisms in the composition is applied in the arable soil attached to the seeds of plants. The microorganisms of the composition are selected from *Azospirillum lipoferum* ssp. lip7R 885*, Azospirillum amazonense* ssp. K21R 887*, Azospirillum irakense* ssp. 5041R 889*, Azospirillum brasilense* ssp. A41R 879*, Azotobacter vinelandii* ssp. ESZ 2132*, Pseudomonas* sp. Szeged 344 O.P. 14*, Pseudomonas fluorescens* var. MOB24, Res24*, Bacillus circulans* var. Res. 97*, Bacillus megaterium* var. Res. 54*, Rhizobium meliloti* var. PolRes. 7*, Alcaligenes faecalis* var. Res36 and PhyllO6-R+32. The strains of the bacteria had been isolated from the environment of different plants and dissimilar soils, then have been made pesticide resistant. The object of the solution according to the patent application is other then the antagonism against the pests of green vegetables.

International patent application No. WO9821964 relates to an individual *Bacillus subtilis* strain, which is capable of inhibiting plant pathogen fungi and bacteria. The *Bacillus subtilis* strain according to the prior art document capable of protecting different plants (fruits, green vegetables) from the infections caused by the pathogens selected from the bacteria and *Botrytis, Fusarium, Phytophthora, Pseudomonas, Erwinia, Alternaria, Trichoderma, Monilinia, Puccinia, Rhizoctonia, Phythium és Plasmopara*. The strain may be applied together with pesticides as well, however suffers from the drawback of lacking copper resistance, therefore the application of copper containing pesticides is excluded in this case.

It can be seen from the above that the solutions according to the state of the art disclose bacteria relevant from the pest control point of view, which can be applied together with pesticides, however, they fail to disclose a copper resistant bacterium strain, which would enable one to use further copper containing pesticides in order to achieve more effective plant protection. Furthermore, there is need for compositions, with which an effective control of the copper resistant plant pathogen bacteria would be achieved. There is need therefore for novel compositions against plant pathogen bacteria and fungi, which would overcome the drawback of the state of the art, especially the application of complicated, multiple step and environmentally stressing pest control technologies. In order to meet these needs we have done systematic research and development, as a result of which we have completed our invention.

DETAILED DESCRIPTION OF OUR INVENTION

Definitions

The term "pest" or "pathogen" as used in the present description means a virus, bacterium or fungus, which lives parasitically in different living organisms, and settling and reproducing in the host or its body (e.g. in a human) causes a disease. The measure of the ability to infect, the pathogenity, may be variable even within one species.

The term "antagonist effect" or "antagonism" as used in the present description means a relationship between microorganisms, in which the members of one species are killed, deterred, or their reproduction is inhibited by the representatives of another species, e.g. through the chemicals (e.g. antibiotics, extracellular enzymes) produced by them.

The term "pest controlling agent" or "pesticide" as used in the present description means a plant protecting agent (chemicals, other agents and a combination of them), whose application intends to kill, exclude, warn off, inhibit or any kind of control pathogen organisms, thereby the effective protection of plants. The pesticide according to the invention may be selected by the skilled person on considering health and safety issues, without undue experimentation.

The term "dose formulation" as used in the present description characterises the type of formulation according to the composition, which is determined according to the *Pesticide formulation types and international coding system catalogue* (Crop-Life International Technical Monography, No. 2; $5^{th}$ Edition, 2002). This may be e.g. aqueous suspension, suspension concentrate, capsulated concentrate, emulsion forming liquid spray, granule, granule dispersible in water, microgranule, water soluble powder, but is not limited thereto. The dose formulation which may be used according to the invention may be selected by the skilled person without undue experimentation.

The term "copper containing pesticide" as used in the present description means a pest control composition, which contains copper. The meaning of the copper containing pesticide is not particularly limited, and it may be selected from the group of copper-sulphate, copper-oxyquinolate, copper-oxide, copper-hydroxide and copper-oxy-chloride. The copper containing pesticide according to the invention may be selected by the skilled person without undue experimentation.

The term "excipient" as used in the present description is not particularly limited, and the excipients may be selected from the group as follows:

a) in case of a liquid formulation e.g. water or an organic solvent (e.g. xilene, methanol, ethylene-glycol or mineral oil), a dispersion stabilizator, a surfactant (e.g. calcium-dodecyl-benzene-sulphonate, polyglycol-ether, etoxylated alkyl-phenol or alkyl-aryl-sulphonates), optionally waxes, b) in case of a granular formulation montmorillonite, bentonite, wood flour, starch, cellulose and a binder, such as e.g. a mineral oil, polyvinyl-alcohol or saccharose, c) and other in itself known, usual additive and/or excipient.

The excipient according to the invention may be selected by the skilled person without undue experimentation.

The Discovery According to the Invention

As a result of the systematic experimental work directed to the present invention we have surprisingly found that the *Bacillus mojavensis* R3B mutant strain a) exerts stronger antagonist effect against pathogens, b) carries copper resistance and c) induces resistance against pathogens in plants unlike/as compared to the state of the art.

Detailed Description Of The Invention

Based on the above, the present invention relates in its first aspect to a biological material for exerting antagonism against vegetable pathogens, which contains *Bacillus mojavensis* R3B mutant strain deposited under # NCAIM (P) B 001389 according to the Budapest Treaty. The biological material according to the invention is an effective antagonist against the pathogens of vegetables, preferably tomato, pepper, lettuce and/or cabbage, in particular against the pathogens selected from the group of *Xanthomonas vesicatoria, Pseudomonas syringae* and *Clavibacter michiganensis* vegetable pathogen bacteria and *Pythium debaryanum, Phytophthora infestans, Alternaria alternata* and *Fusarium oxysporum* vegetable pathogen fungi.

Although we do not wish to restrict the explanation of the antagonist effect according to the present invention to one theory, it can be seen that the unique effect of the biological material according to the invention against the pathogens is on one hand inhibits the operation of pathogens in the rhysosphere of the plants and on the other hand, at the same time it induces resistance in the protected plant against the inhibited pathogens.

In the second aspect, the present invention relates to a composition that comprises a culture of the biological material according to the invention and optionally a copper-containing pesticide, preferably copper-sulphate, copper-oxyquinolate, copper-oxide, copper-hydroxide or copper-oxy-chloride, and optionally an excipient.

Based on the above, the copper-containing pesticide according to the present invention is not particularly limited, in condition that it does not kill the biological material according to the invention, or does not inhibit its operation to an unwanted extent, and such useful copper-containing pesticides include copper-sulphate, copper-oxyquinolate, copper-oxide, copper-hydroxide or copper-oxy-chloride, but are not limited thereto. The pesticide according to the invention may be selected by the skilled person without undue experimentation.

Based on the above, the excipient according to the present invention is not particularly limited, in condition that it does not decrease the effectiveness of the biological material according to the present invention as an active agent, or a biological and chemical active agent combination, and the applicable excipients include without limitation the following:

a) in case of a liquid formulation e.g. water or an organic solvent (e.g. xilene, methanol, ethylene-glycol or mineral oil), a dispersion stabilizator, a surfactant (e.g. calcium-dodecyl-benzene-sulphonate, polyglycol-ether, etoxylated alkyl-phenol or alkyl-aryl-sulphonates), optionally waxes, b) in case of a granular formulation montmorillonite, bentonite, wood flour, starch, cellulose and a binder, such as e.g. a mineral oil, polyvinyl-alcohol or saccharose, c) and other in itself known, usual additive and/or excipient.

The excipient according to the invention may be selected by the skilled person without undue experimentation.

The dose form according to the present invention is not particularly limited, provided that it is suitable for the application of the biological material according to the invention as active agent, or the composition containing said biological material according to the invention to the protected plant or any part thereof. Such applicable dose forms include without limitation the following: aqueous suspension, suspension concentrate, capsulated concentrate, emulsion forming liquid spray, granule, granule dispersible in water, microgranule, water soluble powder. The dose formulation which may be used according to the invention may be selected by the skilled person without undue experimentation.

In its third aspect the invention relates to a process for controlling vegetable pathogens according to which the biological material or composition according to the invention is applied to a plant, preferably to a vegetable, more preferably to tomato, pepper, lettuce and/or cabbage. The biological material according to the invention is preferably applied to the seeds of the protected plant, roots of the protected plant, stem of the protected plant, leaves of the protected plant, blooms of the protected plant, the foliage of the protected plant or fruits of the protected plant, is mixed to the irrigation water of the plant and/or sprayed to the protected plant.

Finally, the invention relates to the use of the biological material or composition according to the invention for the control of pests, preferably for the control of the pests of vegetables, more preferably for the control of the pests of tomato, pepper, lettuce and/or cabbage, furthermore, for inducing resistance in said plants against the pathogens according to the present invention.

EXAMPLES

In the following, our invention is further detailed through preparation and working examples, referring to the figures listed below, annexed to the description.

THE ISOLATION OF *BACILLUS MOJAVENSIS* B5 STRAIN

Figure 1:
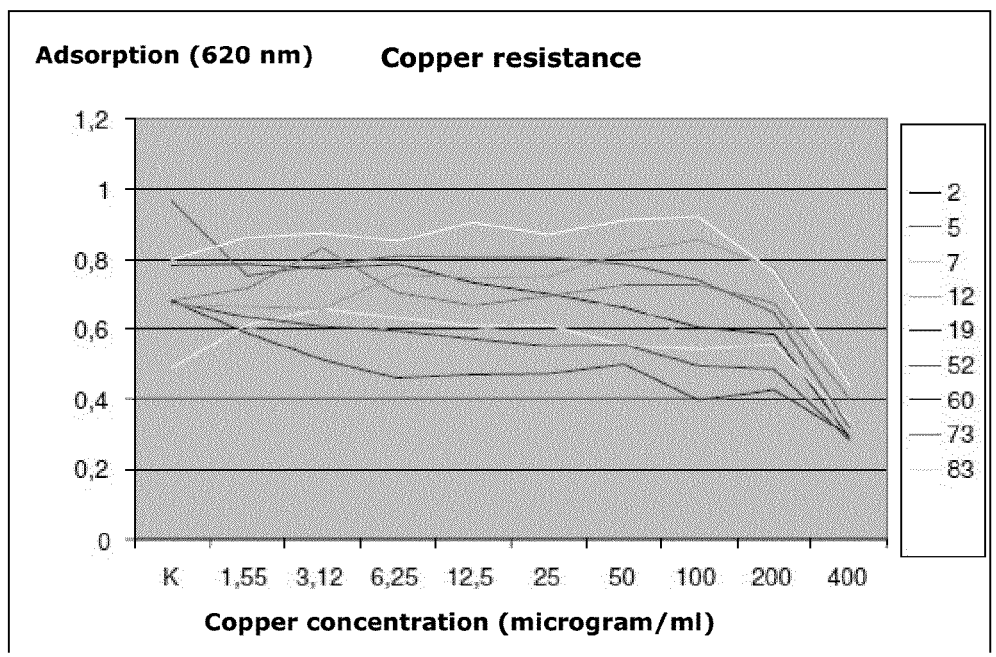
FIG. 1 shows the copper-ion sensitivity results of the strains showing excellent antagonist capability in the widest spectrum.
Figure 2:
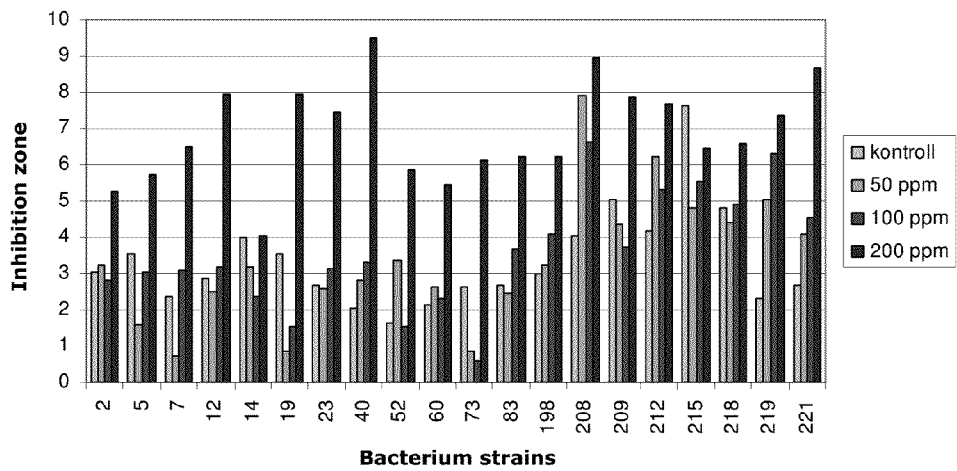
FIG. 2 shows the antagonist activity of 20 bacterium strains as a function of the copper concentration.
Figure 3:
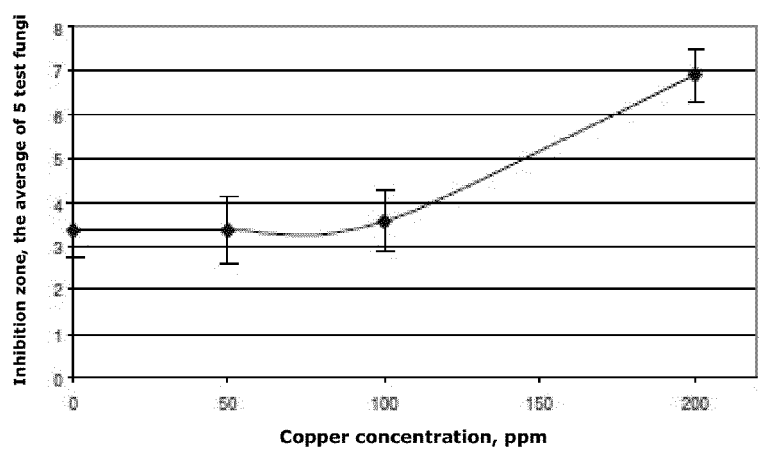
FIG. 3 shows the change of the antagonist effect against fungi as a function of the copper concentration, an average of 20 strains.

In the course of our experiments we have tested the antagonist ability of 82 endophyte bacterium strains and 44 bacterium strains isolated from the rhysosphere, then we have selected the best 20 antagonist strains, and their antagonist abilities have been tested in the presence of copper. Among the best antagonist 10 copper-resistant *Bacillus* strains, the *Bacillus mojavensis* B5 strain possessed the best antagonist features, especially the R3B copper-resistant mutant strain, which is the subject matter of our claim for the protection.

The Isolation of Dominant Bacterium Strains from the Rhysosphere and Roots of the Produced Plants, and Testing of their Antagonism The isolations were made from the root surface and rhizomes of different tomato and pepper species on bacterium selective culturing medium. 10-10 strains were isolated from the dominant colony types in case of each tested sample. The best antagonists were selected against *Pseudomonas syringae, Xanthomonas vesicatoria, Erwinia carotovora*, illetve *Phytophthora infestans, Sclerotinia sclerotiorum, Alternaria solani* and *Botrytis cinerea* with preliminary antagonism tests on culturing plates. These were identified on species level by partial sequencing their 16S RNS gene, in order to exclude the plant pathogens from the further examinations. The efficacy of the non pathogenic strains was tested against another plant pathogenic bacteria and fungi. 40 of the best antagonists were selected for the in vivo plant treatment examinations.

Isolation and Testing of the Endophyte Bacteria 82 endophyte bacterium strains were isolated from the roots and seeds of different vegetables (parsley, carrot, tomato, pepper, white cabbage, lettuce, spring onion, cucumber). Their ability to antagonize the plant pathogen *Fusarium oxysporum, Rhizoctonia solani; Xanthomonas campestris* pv *vesicatoria, Erwinia carotovora* and *Pseudomonas syringae* strains was tested by in vitro antagonism tests. The antagonist potential of the best 10 strains was tested against the plant pathogen fungi *Phytophtora infestans, Botrytis cinerea, Sclerotinia sclerotiorum* and *Alternaria tenuis* as well. Furthermore, the effect of pH on the growth was tested: it was determined, which strains can grow at pH=5.5. This has importance in their applicability in more acidic soils. Preliminary copper tolerance test were made with the strains (this is important for the reason of their applicability in the integrated pest control) with culturing media containing 25 and 50 microgram/ml $CuSO_4$, and found that 71 and 49 strains grew in the tested values. To determine the strains, the 16S RNS gene was amplified by PCR (primers: Eub8F és Eub534R), sequenced, then compared with the databases to exclude plant or human pathogen strains. 10 good antagonist bacteria were used for the plant tests out of the 82 original endophyte bacteria.

The Examination of the Bacterium Strains Isolated from the Rhyzosphere

Samples were taken from a greenhouse, from the rock wool of tomato plants grown in a hydroponic system, and 39 strains were isolated on a culture medium buffered to pH=5.5. Their antagonism was tested against *Fusarium oxysporum, Phytophtora infestans, Botrytis cinerea, Sclerotinia sclerotiorum, Alternaria tenuis, Clavibacter michiganense, Xanthomonas campestris* pv *vesicatoria* and *Pseudomonas syringae*.

From 10 samples originating from arable soil 44 strains were isolated on a pH=5.5 culture medium, 28 strains with the ability to grow in cold conditions, and 27 strains on a *Pseudomonas* selective culturing medium using *Bacillus* strain selective methods. These strains were tested against *Clavibacter michiganense, Xanthomonas campestris* pv *vesicatoria* and *Pseudomonas syringae* by in vitro antagonism tests. To determine the strains, the 16S RNS gene was amplified by PCR (primers: Eub8F és Eub534R), sequenced, then compared with the databases to exclude the plant or human pathogen strains.

The Preparation of Copper-Resistant Mutants from the Bacterium Strains Showing Excellent Antagonism The copper-ion sensitivity of the strains showing excellent antagonism in the widest spectrum was determined by culturing medium dilution method (FIG. 2). Then strains were prepared with a copper-ion tolerance exceeding 200 μg/ml by selection for spontaneous copper-resistance.

The test was made with 20 pre-selected strains: B2, B5, B7, B12, B14, B19, B23, B40, B52, B60, B73, B83, B198, B208, B209, B212, B215, B218, B219, B221. The strains were maintained on peptone culturing medium at +5° C. temperature, for prolonged shelf life on YDC culturing medium, also at +5° C. temperature. The tests, as the majority of the following tests, were made on peptone culturing medium or liquid. The copper tolerance of the strains was tested on a culturing medium containing 10, 20, 40, 100 and 200 ppm copper. The copper was admixed to the culturing medium in the form of copper-sulphate, starting from 10000 ppm stock solution, calculating the concentration for the copper active agent. The fresh culture of the bacteria was used to prepare a $10^6$/ml suspension, and 100 μl of this was transferred into 9 cm Petri dishes. The evaluation was made continuously, 2-3 days afterwards. In the test made in the culturing liquid 10 μl of the bacterium suspension with the same concentration was added to 10 ml culturing liquid. The evaluation was made 2 days afterward, by measuring of the optical density (660 nm), and confirmed by Bürker camera. The incubation was done in each case at a temperature of 22-25° C., in dark.

All 20 strains grew both on the culturing medium and in the culturing liquid even with 200 ppm copper concentration, and no significant difference was revealed as compared to the growth at lower copper concentration.

In the following tests the copper concentration of the culturing medium was increased to 400 and 800 ppm, respectively. At 400 ppm the B5, B198, B208, B219 és B221 strains showed no growth anymore, the others still grew in a small compass. The 800 ppm concentration resulted in complete inhibition. At the same time, transferring to a culturing medium of 400, then 800 ppm copper concentration, colonies from each strain were isolated which were able to grow in such a high concentration, and they could be maintained in a culturing medium with said copper concentration. As the 400 and in particular 800 ppm copper concentration is higher than the value necessary to inhibit the growth of plant pathogen fungi and bacteria, further, which may appear in soils, it was not reasonable to isolate strains tolerant with even higher copper concentration. The copper tolerant strains were maintained on a culturing medium containing 800 ppm copper at +5° C. temperature.

The Antagonism Against Plant Pathogens, the Effect of Copper on the Antagonism

The tests were made with the above 20 bacterium strains, against the following plant pathogens:

*Pseudomonas syringae* (5 strains)
*Pythium ultimum*
*Phytophthora infestans* (3 strains)
*Sclerotinia sclerotiorum*
*Fusarium oxysporum* fsp. *lycopesici*
*Alternaria solani*
*Rhizoctonia solani*

The antagonism tests were made on a peptone agar, on PDA, which is more suitable for fungi, and in case of *Phytophthora* strains on pea agar, supplementing the culturing medium with 0, 50, 100 és 200 ppm copper. The antagonist bacterium strains were inoculated starting from a fresh culture, using a 5 mm diameter filter paper disc, into one third of the 9 cm culturing medium disc, at the same time, in front of them into the second third of the culturing medium disc the plant pathogen *Pseudomonas* strains were inoculated by a similar method, furthermore, the fungi were inoculated using a 5 mm diameter mycelium disc cut off the fresh culture. The incubation took place in each case at a temperature of 22-25° C., in dark.

The evaluation was started 2 days afterwards, and was made continuously, measuring the appeared inhibition zones. The evaluation of the results was done by one and two factor analysis of varience.

From the results in can be seen that there were significant differences between the antagonist bacterium strains regarding the antagonism showed against the fungi pathogens (*Pythium* and genuine fungi), however, in the culturing medium containing copper this difference was insignificant ($p=0.05$). At the same time the difference grew further upon the addition of 50 ppm copper, and 100 and 200 ppm resulted in significant difference between the strains (FIG. 2).

The addition of copper slightly increased the antagonist activity, however, the difference on average of five test fungi (*P. ultimum, S. sclerotiorum, A. solani, F. oxysporum* és *R. solani*) was significant only at 200 ppm copper concentration (FIG. 3). At the same time, it is worth mentioning that this concentration significantly increased the growth of the test fungi, and made it difficult to evaluate the results. In cases of B2, B5, B7, B12, B19, B23, B40, B52, B60, B73, B83, B198, B208, B209, B219 and B221 strains a definitely stronger antagonist effect was experienced within such circumstances, however, at lower concentrations (50 és 100 ppm) this phenomenon was seen only with the B208, B219 és B221 strains (FIG. 2).

Considering the average sensitivity of the above-mentioned five test fungi against the antagonists, there were of course significant differences, and these differences were significant at every copper concentration, and even without copper. *F. oxysporum* and *R. solani* were proved to be the least sensitive, in these cases the sensitivity was not even increased by the elevation of the copper concentration. *A. solani* was moderately sensitive as well, but the copper concentration of 200 ppm resulted in a significant increase in the sensitivity. *P. ultimum* and the tested *S. sclerotinia* strains were more sensitive, especially with high copper concentration.

The reaction of the tested plant pathogen *P. syringae* bacteria was significantly different from the pathogen fungi. There was not any significant difference in the effectiveness of the 20 antagonist bacteria considering the average of the 5 *P. syringae* strains. Similarly, there was no significant difference between the sensitivity of the different *P. syringae* strains. Unlike the experiences with the plant pathogen fungi, the copper content of the culturing medium definitely decreased the effectiveness of the antagonists. The difference experienced was significant only at 100 and 200 ppm copper concentration. (The copper sensitivity of the plant pathogen *P. syringae* strains was approximately the same as that of the 20 antagonist bacteria: all increased at 200 ppm concentration, and none of them at 400 ppm.)

The *Phytophthora infestans* strains involved in the test were more sensitive to the copper ions as compared with the other pathogens, they did not show growth anymore at 100 ppm concentration, therefore the tests were made only at 50 ppm concentration. There was significant difference between the efficacies of the antagonist bacteria, however, the presence of copper did not result in significant change (it was similar to the other tested fungi, where there was no clear change in the character of the antagonist activity at 50 ppm copper concentration).

As to the influence of the copper ions on the efficacy of the antagonists, it was established that the enhancement of the efficacy that may be used in the further tests was experienced only in cases of plant pathogen fungi and only at a relatively high (200 ppm) copper ion concentration.

Greenhouse and Field Tests with the Promising Bacterium Strains

Greenhouse and field treatment tests were made with the copper-resistant strains proven to be the best antagonist. The tests aimed at clarifying the rhysosphere tolerance of the anatagonist strains in tomato and pepper culture (culturing methods using soil or using no soil), and in other vegetable cultures (cabbage, lettuce), and especially the very important question of how the plant tolerates the treatment with the bacterium. Using quantitative culturing from the rhizomes of the treated plants it was clarified if the bacterium strain is incorporated in the plant, if it makes colonies endogenously without adversely affecting the development of the plant. The tests were run with 20 strains possessing excellent in vitro antagonism spectrum.

The tests were made in two periods, using 2×10 bacterium strains. The strains to be tested (members of the *Bacillus, Pseudomonas, Pantoea* genus) were diluted to the required concentration, and the production boxes and the rock wool sowing platform were irrigated with this solution immediately after sowing. The further tests were made with young plants already having leaves. The plant samples were collected at two dates, where the leaves of the selected plants were counted, and the plants were collected without their roots and their fresh green mass was weighed. The tests were made with pepper and tomato species, in soil and rock wood production system, considering the irrigation with three different bacterium concentrations. In cases of cabbage and lettuce the tests were set only to the soil production method. All tests were made in four sets, in random block arrangements.

10 *Bacillus* strains have proven to be the best.

Greenhouse and Field Tests II. Testing of the Ability to Induce Resistance

Regarding the antagonist bacterium component according to our planned compositions it is an important requirement that it should provide protection against the bacterial and fungal pathogens not only at the *rhizosphere*, but also at the organs of the plants above the soil through the activation of the inducible resistance mechanisms of the plant. The tests were made with tomato and pepper. The roots of the young plants were treated with the suspension of the antagonist bacterium strains, and after planting, when different intervals in time have passed, artificial infections were provoked on the leaves with a cell and conidium suspension of the plant pathogen bacteria and fungi. Furthermore, it was evaluated how the level of the chemicals playing important role in the induced resistance changes in the treated plants as compared with the control (reference) plants.

Figure 5:
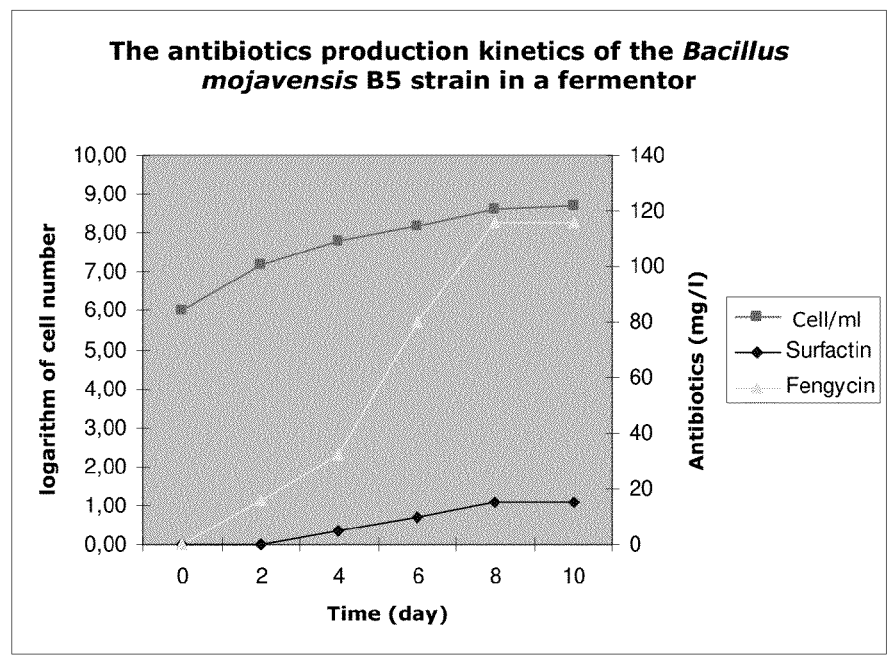
FIG. 5 shows the antibiotics production kinetics of the *Bacillus mojavensis* B5 strain in a fermentor.
Figure 6:
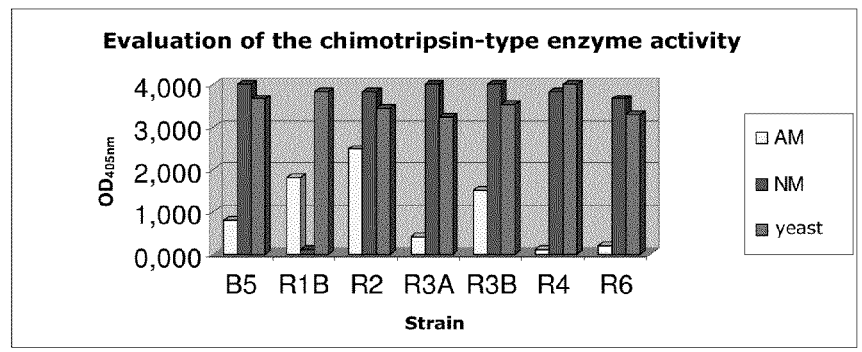
FIG. 6 shows the ability of the *Bacillus mojavensis* B5 and the copper-resistant mutants made therefrom to produce extracellular protease.
Figure 7:
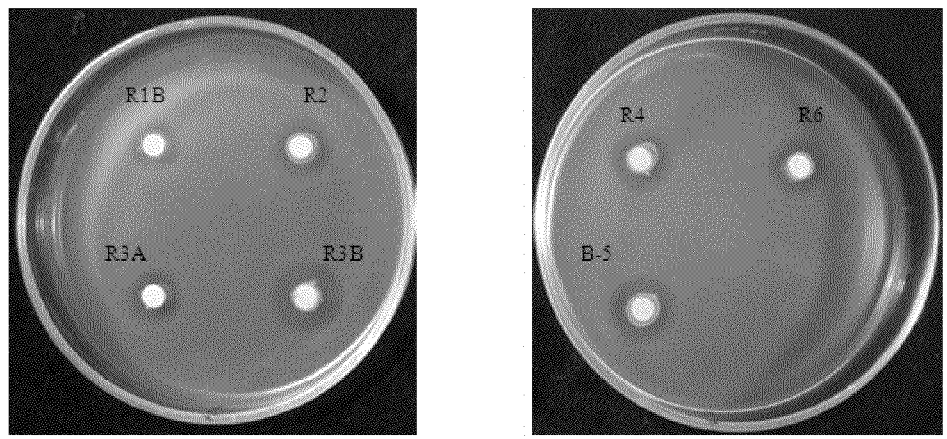
FIG. 7 shows the inhibition of *Pseudomonas syringae* by the a *Bacillus mojavensis* B5 and the copper-resistant mutants made therefrom.

Our excellent antagonist B5 *Bacillus* strain had the ability to induce the self-protection mechanism of the plant [Systemic Acquired, Resistance, (SAR)]. The R3B copper resistant mutant spontaneously appearing after transferring of the *Bacillus mojavensis* B5 strain onto a culturing medium containing 400 ng/ml copper-sulphate was proven to be the best. This strain possesses wide spectrum and excellent antagonist abilities probably for the reason of secreting in large amount an antifungal depsi-peptide antibiotics, fengycin (FIG. 5), and the constitutive chimotripsin type protease, which enhances the effect through synergism (FIG. 6).

Evaluation of the Antibiotics and Chimotripsin Production of the *Bacillus mojavensis* B5 Strain and the Copper Resistant Mutants Made Therefrom The strains were maintained by weekly cross inoculation, on YEG culturing plates (0.2% glucose, 0.2% yeast extract, 2% baktoagar). For the antibiotics production tests mainly minimal culturing solution was used suitably changing the used carbon and nitrogen source, furthermore the concentration of the two trace elements (iron and copper). This culturing solution, unlike e.g. a yeast extract based culturing solution, does not contain amino acids and peptides, thus the analysis and purification of the antibiotics mixtures secreted into the fermenting liquid can be made more easily.

Based on the preliminary production experiences, the following GGM culturing solution was used:

| | |
|---|---|
| Glucose | 1% |
| Glutaminic acid Na salt | 0.5% |
| $KH_2PO_4$ | 0.1% |
| $K_2HPO_4$ | 0.1% |
| $MgSO_4 \times 7H_2O$ | 0.05% |
| KCl | 0.1% |
| $FeSO_4 \times 7H_2O$ | 10 mg/l |
| $CuSO_4 \times 5H_2O$ | 1 mg/l |

20 ml culturing solution was measured into 50 ml Erlenmeyer flasks. After inoculation the culturing took place on an orbital shaking device for 6 days, at 180 rpm and 25° C. temperature.

The cell density of the cultures was determined by measuring the absorption at 620 nm. In case of the *Bacillus* strains a 0.1 OD value is equivalent with a $10^7$ cell/ml concentration. Thereafter the bacterium cells were settled by centrifuging at 8000 G for 10 minutes, and the supernatant was transferred to a beaker, then the pH of the fermented liquids was set to 2 using 10% hydrochloric acid (0.4 ml to 20 ml fermented liquid). The precipitated fermented liquids were incubated at 5° C. temperature overnight, to complete the precipitation. Then the precipitate was settled by centrifugation, and dissolved in 1 ml 96% ethanol.

The Quantitative Determination of the Antibiotics from the Ethanol Preparations

The fengycin molecule contains 2 tyrosine molecules, which however shows a strong absorbance at 280 nm. Thus, the antibiotics content other than surfactin of the antibiotics preparations may be estimated by measuring at 280 nm. Thus, all OD of the ethanol preparations diluted to 10 times of their original concentration was measured at 280 nm.

Thin Layer Chromatograpy (TLC) of the Secreted Antibiotics

Figure 4:
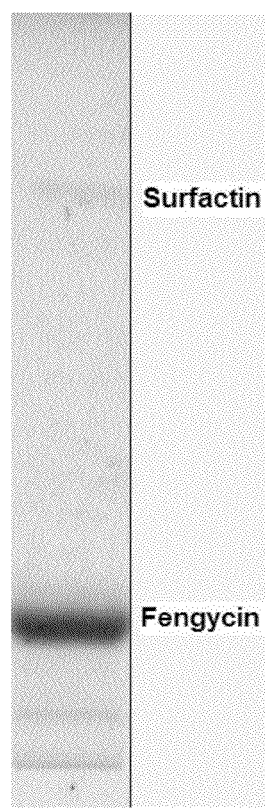
FIG. 4 shows the thin layer chromatograpy of the antibiotics spectrum secreted by the *Bacillus mojavensis* B5 strain.

In our preliminary studies, as well as in the tests of the novel strains in the thin layer chomatograpic analysis of the strains a glutaminic acid/glucose culturing solution was used, as in cases of most strains this provided the sufficient yield of antibiotics. FIG. 4 shows the results of the TLC analysis of the fermented liquid of the B5 strain.

In the course of the pest control application it is extremely important to use the suitable culturing medium when preparing the cultures. The results prove that the above-mentioned glutaminic acid/glucose culturing solution should be used, as the culture may be diluted even to 10-20 times of its original volume, and even in this case the fengycin concentration/ml is 10-12 mg/l, which achieves a complete inhibition of the majority of the plant pathogen fungi, and is sufficient to activate the induced resistance mechanism in the treated plant.

The Antagonist Ability of the *B. mojavensis* B5 Strain and the Copper Resistant Mutants Spontaneously Produced Therefrom The strains were cultured on a yeast extract culturing medium for 48 hours. The inhibition of *Pseudomonas syringae, Clavibacter michiganensi* and *Xanthomonas campestris* by the B5 strain and its copper resistant mutants was tested. It can be seen in the table that the best inhibiting effect is possessed by the R3B copper resistant mutant.

| Inhibition zone (mm) | | | | | | | |
|---|---|---|---|---|---|---|---|
| | B-5 | R1B | R2 | R3A | R3B | R4 | R6 |
| *Pseudomonas syringae* | 3.0 | 2.0 | 4.0 | 3.0 | 5.0 | 2.0 | 3.0 |
| *Clavibacter michiganensis* | 6.0 | 2.0 | 3.0 | 6.0 | 7.0 | 5.0 | 4.0 |
| *Xanthomonas campestris* | 7.0 | 5.0 | 6.0 | 7.0 | 7.0 | 7.0 | 8.0 |

The copper-resistant B5 strains' inhibition effects on *Fusarium osysporum* was compared to the parent strain. The table shows that in this case also the R3B copper resistant mutant possesses the best efficacy. Therefore, we seek protection for this strain.

| Inhibition zone (mm) | | | | | | | |
|---|---|---|---|---|---|---|---|
| | B-5 | R1B | R2 | R3A | R3B | R4 | R6 |
| *Fusarium oxysporum* | 3.5 | 3.5 | 3.0 | 4.0 | 4.0 | 3.5 | 4.5 |

INDUSTRIAL APPLICABILITY OF THE INVENTION

It is a benefit of the present invention that the isolated *Bacillus mojavensis* R3B mutant strain induces a strong antagonist effent against pathogens, and also carries copper-resistance and has the ability to activate an induced resistance in plants against the pathogens. Due to its copper-resistant feature, it may be used together with copper containing pesticides, thus may effect an integrated pest control.

What is claimed is:

1. A biological material for exerting antagonism against vegetable pathogens, which contains *Bacillus mojavensis* R3B mutant strain deposited under # NCAIM (P) B 001389 according to the Budapest Treaty.

2. A process for controlling pathogens, said process comprising applying the biological material according to claim 1 to a plant.

3. The process according to claim 2, said process comprising applying the biological material to a) seeds of the plant,
b) roots of the plant,
c) stems of the plant, or
d) leaves, flowers, foliage or fruits of the plant, by mixing the biological material with irrigation water of the plant and/or spraying the biological material to the plant.

4. The process of claim 2, wherein the pathogens are pathogens of tomato, pepper, lettuce or cabbage.

5. The process of claim 2, wherein the plant is a vegetable.

6. The process of claim 2, wherein the plant is tomato, pepper, lettuce or cabbage.

7. The process according to claim 2, wherein the pathogens are pathogens of green vegetables.

8. The process according to claim 2, wherein the pathogens are selected from the group consisting of *Xanthomonas vesicatoria, Pseudomonas syringae* and *Clavibacter michiganensis* plant pathogen bacteria and *Pythium debaryanum, Phytophthora infestans, Alternaria alternate* and *Fusarium oxysporum* plant pathogen fungi.

9. A pesticide composition, which contains a culture of the biological material according to claim 1, and contains a copper-containing pesticide, and optionally an excipient.

10. The composition according to claim 9, which is in an aqueous suspension, suspension concentrate, capsulated concentrate, emulsion forming liquid spray, granule, granule dispersible in water, microgranule or water soluble powder dose formulation.

11. The pesticide composition of claim 9, wherein the copper-containing pesticide is selected from the group consisting of copper-sulphate, copper-oxyquinolate, copper-oxide, copper-hydroxide and copper-oxy-chloride.

12. A process for controlling pathogens, said process comprising applying the pesticide composition of claim 9 to a plant.

13. The process according to claim 12, said process comprising applying the pesticide composition to a) seeds of the plant,
b) roots of the plant,
c) stems of the plant, or
d) leaves, flowers, foliage or fruits of the plant, by mixing the biological material with irrigation water of the plant and/or spraying the biological material to the plant.

14. The process of claim 12, wherein the plant is a vegetable.

15. The process of claim 12, wherein the plant is tomato, pepper, lettuce or cabbage.

16. The process according to claim 12, wherein the pathogens are pathogens of green vegetables.

17. The process of claim 12, wherein the pathogens are pathogens of tomato, pepper, lettuce or cabbage.

18. The process according to claim 12, wherein the pathogens are selected from the group consisting of *Xanthomonas vesicatoria, Pseudomonas syringae* and *Clavibacter michiganensis* plant pathogen bacteria and *Pythium debaryanum, Phytophthora infestans, Alternaria alternate* and *Fusarium oxysporum* plant pathogen fungi.

* * * * *